(12) United States Patent
Yang

(10) Patent No.: US 7,491,227 B2
(45) Date of Patent: Feb. 17, 2009

(54) COILED-SHEET STENT WITH FLEXIBLE MESH DESIGN

(75) Inventor: Yi Yang, San Francisco, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/462,876

(22) Filed: Jun. 16, 2003

(65) Prior Publication Data

US 2004/0254630 A1 Dec. 16, 2004

(51) Int. Cl.
*A61F 2/06* (2006.01)
(52) U.S. Cl. .................................... 623/1.15
(58) Field of Classification Search ....... 623/1.15–1.22, 623/1.34
See application file for complete search history.

(56) References Cited

U.S. PATENT DOCUMENTS

| | | | |
|---|---|---|---|
| 3,868,956 | A | 3/1975 | Alfidi et al. |
| 4,503,569 | A | 3/1985 | Dotter |
| 4,512,338 | A | 4/1985 | Balko et al. |
| 4,565,589 | A | 1/1986 | Harrison |
| 4,631,094 | A | 12/1986 | Simpson et al. |
| 4,762,128 | A | 8/1988 | Rosenbluth |
| 4,795,458 | A | 1/1989 | Regan |
| 4,830,003 | A | 5/1989 | Wolff et al. |
| 4,950,277 | A | 8/1990 | Savin et al. |
| 4,994,071 | A | 2/1991 | MacGregor |
| 5,007,926 | A * | 4/1991 | Derbyshire ................. 623/1.15 |
| 5,019,085 | A | 5/1991 | Hillstead |
| 5,035,706 | A | 7/1991 | Giantureo et al. |

(Continued)

FOREIGN PATENT DOCUMENTS

WO WO 00/61034 A1 10/2000

(Continued)

OTHER PUBLICATIONS

P.H. Bureister, et al., PCT Publication No. WO/95/31945, "Improved Tissue Supporting Devices", Nov. 30, 1995.

(Continued)

*Primary Examiner*—Suzette J Gherbi
(74) *Attorney, Agent, or Firm*—Vidas, Arrett & Steinkraus

(57) ABSTRACT

A coiled-sheet stent includes a tubular body having a longitudinal axis and a circumference, and a plurality of cylindrical bands formed in the tubular body, each band having a zig-zag pattern including a series of sequential diagonal elements connected to one another and extending about the circumference. A plurality of longitudinal connectors extend between and connect adjacent bands. The diagonal elements have an arcuate shape, all diagonal elements in each band being oriented in either a clockwise or counter-clockwise direction about the circumference. The tubular body is expandable between contracted and enlarged conditions, and the zig-zag pattern is expandable between unstretched and unstretched conditions, the zig-zag pattern being biased towards the stretched condition above a transition temperature, thereby at least partially defining the enlarged condition. A multi-cellular stent structure is also provided that includes a plurality of bat shaped cells formed in a tubular body, each cell defining a head region, a tail region and opposing curved wing regions, and a plurality of connectors extending between and connecting adjacent cells. The head and tail regions of adjacent cells are directly connected to one another, and connectors extend between adjacent wing regions of adjacent cells.

20 Claims, 4 Drawing Sheets

U.S. PATENT DOCUMENTS

| | | | |
|---|---|---|---|
| 5,037,427 A | 8/1991 | Harada et al. | |
| 5,089,005 A | 2/1992 | Harada | |
| 5,100,429 A | 3/1992 | Sinofsky et al. | |
| 5,102,417 A | 4/1992 | Palmaz | |
| 5,135,536 A | 8/1992 | Hillstead | |
| 5,158,548 A | 10/1992 | Lau et al. | |
| 5,167,614 A | 12/1992 | Tessmann et al. | |
| 5,197,978 A | 3/1993 | Hess | |
| 5,282,824 A | 2/1994 | Gianturco | |
| 5,330,500 A | 7/1994 | Song | |
| 5,354,308 A | 10/1994 | Simon et al. | |
| 5,356,423 A | 10/1994 | Tihon et al. | |
| 5,395,390 A | 3/1995 | Simon et al. | |
| 5,405,377 A | 4/1995 | Cragg | |
| 5,441,515 A * | 8/1995 | Khosravi et al. | 606/194 |
| 5,443,498 A | 8/1995 | Fontaine | |
| 5,443,500 A * | 8/1995 | Sigwart | 623/1.17 |
| 5,449,373 A | 9/1995 | Pinchasik et al. | |
| 5,466,242 A | 11/1995 | Mori | |
| 5,197,978 A | 5/1996 | Hess | |
| 5,540,712 A | 7/1996 | Kleshinski et al. | |
| 5,556,413 A | 9/1996 | Lam | |
| 5,562,641 A | 10/1996 | Flomenblit et al. | |
| 5,597,378 A | 1/1997 | Jervis | |
| 5,618,299 A | 4/1997 | Khosravi et al. | |
| 5,624,508 A | 4/1997 | Flomenblit et al. | |
| 5,643,312 A | 7/1997 | Fischell et al. | |
| 5,649,952 A | 7/1997 | Lam | |
| 5,649,977 A | 7/1997 | Campbell | |
| 5,665,115 A | 9/1997 | Cragg | |
| 5,683,450 A | 11/1997 | Goicoechea et al. | |
| 5,728,150 A | 3/1998 | McDonald et al. | |
| 5,733,303 A | 3/1998 | Israel et al. | |
| 5,733,330 A | 3/1998 | Cox | |
| 5,746,765 A | 5/1998 | Kleshinski et al. | |
| 5,755,734 A | 5/1998 | Richter et al. | |
| 5,766,237 A | 6/1998 | Cragg | |
| 5,776,183 A | 7/1998 | Kanesaka et al. | |
| 5,788,979 A | 8/1998 | Alt et al. | |
| 5,800,520 A | 9/1998 | Fogarty et al. | |
| 5,807,404 A | 9/1998 | Richter | |
| 5,824,045 A | 10/1998 | Alt | |
| 5,824,052 A | 10/1998 | Khosravi et al. | |
| 5,824,054 A | 10/1998 | Khosravi et al. | |
| 5,833,707 A | 11/1998 | McIntyre et al. | |
| 5,836,964 A | 11/1998 | Richter et al. | |
| 5,843,117 A | 12/1998 | Alt et al. | |
| 5,843,120 A | 12/1998 | Israel et al. | |
| 5,843,175 A | 12/1998 | Frantzen | |
| 5,843,176 A | 12/1998 | Weier | |
| 5,855,600 A | 1/1999 | Alt | |
| 5,860,999 A | 1/1999 | Schnepp-Pesch et al. | |
| 5,868,782 A | 2/1999 | Frantzen | |
| 5,871,437 A | 2/1999 | Alt | |
| 5,871,538 A | 2/1999 | Dereume | |
| 5,876,434 A | 3/1999 | Flomenblit et al. | |
| 5,882,444 A | 3/1999 | Flomenblit et al. | |
| 5,895,406 A | 4/1999 | Gray et al. | |
| 5,902,317 A | 5/1999 | Kleshinski et al. | |
| 5,954,743 A | 9/1999 | Jang | |
| 5,964,770 A | 10/1999 | Flomenblit et al. | |
| 5,972,018 A | 10/1999 | Israel et al. | |
| 5,976,182 A | 11/1999 | Cox | |
| 6,007,573 A | 12/1999 | Wallace et al. | |
| 6,015,433 A | 1/2000 | Roth | |
| 6,017,365 A | 1/2000 | Von Oepen | |
| 6,042,605 A | 3/2000 | Martin et al. | |
| 6,048,360 A | 4/2000 | Khosravi et al. | |
| 6,086,610 A | 7/2000 | Duerig et al. | |
| 6,174,329 B1 * | 1/2001 | Callol et al. | 623/1.34 |
| 6,193,747 B1 | 2/2001 | Von Oepen | |
| 6,244,626 B1 | 5/2001 | Steinke | |
| 6,290,720 B1 | 9/2001 | Khosravi et al. | |
| 6,547,818 B1 * | 4/2003 | Rourke et al. | 623/1.16 |
| 6,723,120 B2 * | 4/2004 | Yan | 623/1.15 |
| 6,793,672 B2 * | 9/2004 | Khosravi et al. | 623/1.13 |
| 7,122,059 B2 | 10/2006 | Rourke et al. | |
| 2003/0144725 A1 * | 7/2003 | Lombardi | 623/1.13 |
| 2005/0049687 A1 | 3/2005 | Yang et al. | |

FOREIGN PATENT DOCUMENTS

| | | |
|---|---|---|
| WO | WO 01/01885 A1 | 1/2001 |
| WO | WO 01/32099 A2 | 5/2001 |
| WO | WO 02/34162 A2 | 5/2002 |

OTHER PUBLICATIONS

Pierre Hilaire, PCT Publication No. WO/98/58600, "Expandable Stent with Variable Thickness", Dec. 30, 1998.

Jean-Claude Sgro, EPO Publication No. 0 566 807 A1, Oct. 27, 1993.

Giovanni Rolando, et al., EPO Publication No. EP 0 806 190 A1, "An Angioplasty Stent," Nov. 12, 1997.

Timothy J. Ley, et al., PCT Publication No. WO/99/44543, "Improved Stent Cell Configurations," Sep. 10, 1999.

Randolf Van Oepen, PCT Publication No. WO/98/35634, "Stent," Aug. 20, 1998.

F. Khosravi, et al., PCT Publication No. WO 99/48441, "Coiled Sheet Graft for Single and Bifurcated Lumens and Methods of Makng and Use", Sep. 30, 1999.

F. Khosravi, et al., PCT Publication No. WO 00/28921, "Coiled-Sheet Stent-Graft with Exo-Skeleton", May 25, 2000.

Ulrich Sigwart, EPO Publication No. 0 382 014 B1, "Intravascular Endoprosthesis," Dec. 14, 1994.

* cited by examiner

COILED-SHEET STENT WITH FLEXIBLE MESH DESIGN

FIELD OF THE INVENTION

The present invention relates generally to prostheses for implantation within body lumens, and more particularly to a coiled-sheet stent including a stretchable mesh design.

BACKGROUND

Tubular prostheses or "stents" are often implanted within blood vessels, for example, within the coronary and carotid arteries, for treating atherosclerotic disease which may involve one or more stenoses. Stents generally have a tubular shape capable of assuming a radially contracted condition to facilitate introduction into a patient's vasculature, and an enlarged condition for engaging the vessel wall at a treatment location. In its contracted condition, the stent may be placed on or in a delivery device, such as a catheter, percutaneously introduced into a patient's vasculature and advanced to a target treatment location. Once at the treatment location, the stent may be deployed and expanded to its enlarged condition, thereby engaging the wall of the vessel and substantially anchoring the stent in place.

Plastically deformable stents have been suggested that are initially provided in their contracted condition, and placed over a balloon on an angioplasty catheter. At the treatment location, the balloon is inflated to plastically deform the stent until it is expanded to its enlarged condition. Thus, the stent may be expanded to any size within a specified range to ensure that the stent substantially engages the wall of the vessel. Plastically deformable stents, however, may not expand uniformly and may not provide a desired delivery profile because of the need for a balloon on the delivery device underlying the stent.

Stents have also been suggested that are self-expanding, i.e., that are biased to assume their enlarged condition but may be radially compressed to a contracted condition. The stent may be mounted to a delivery device and constrained in a contracted condition during delivery, for example, by an overlying sheath. At the treatment location, the stent may be released, for example, by retracting the overlying sheath, the stent automatically resuming its enlarged condition to engage the vessel wall. Such stents, however, may not provide as small a delivery profile as desired and may not anchor against the wall of a vessel as securely as desired, which may lead to migration of the stent within the vessel.

In addition to tubular stents, coiled-sheet stents have been suggested. A flat sheet is provided that is rolled into a spiral shape having overlapping inner and outer longitudinal sections that defines a contracted condition. The coiled-up sheet may be biased to at least partially unroll to assume an enlarged condition, and/or may be caused to unroll and radially expand using a balloon. The coiled-sheet stent may have a nondeformable lattice-like structure and a plurality of fingers or teeth along the inner longitudinal section for engaging openings in the lattice.

Once the coiled-sheet stent is deployed at the treatment location and at least partially expands, a balloon may be introduced within the stent and inflated to further expand the stent to a desired enlarged condition. When the balloon is deflated, the stent may try to radially contract, but the fingers on the inner longitudinal section may then engage corresponding openings in the lattice to lock the stent in the enlarged condition.

Coiled-sheet stents may provide enhanced anchoring within the blood vessel because the size of the fully expanded stent may be more precisely controlled. A coiled-sheet stent, however, may be more rigid transverse to its longitudinal axis than tubular stents (depending upon the respective cell structures of the stents), potentially resulting in a less flexible stent, which may not be implanted as effectively in tortuous anatomical conditions. Further, because the lattice-like structure of coiled-sheet stents is substantially nondeformable, if the stent is subjected to radially compressive forces, e.g., when the vessel wall attempts to contract, the stent may tend to buckle rather than recoil from the stress.

Accordingly, there is a need for a stent that provides improved flexibility, while still providing substantial anchoring within a blood vessel.

SUMMARY OF THE INVENTION

The present invention is directed to prostheses for implantation within body lumens, and more particularly to stents including a stretchable mesh design. In accordance with one aspect of the present invention, a stent is provided that includes a generally tubular body having a longitudinal axis and a circumference, and having a size adapted for introduction into a body lumen. A plurality of cylindrical bands are formed in the tubular body, each band having a generally zig-zag pattern including a series of sequential diagonal elements connected to one another and extending about the circumference. A plurality of longitudinal connectors extend between and connect adjacent bands.

The diagonal elements have a generally arcuate shape, all diagonal elements in each band being oriented in either a clockwise or counter-clockwise direction about the circumference for facilitating packing of the diagonal elements in each band with one another. In a preferred form, each diagonal element includes a first member and a second member, each of the first and second members having first and second ends, the second ends being connected together by an elbow, the first ends being connected to preceding and succeeding diagonal elements in the zig-zag pattern. Preferably, the first and second members each have a slight curvature, with the curvature of the first member being opposite to the curvature of the second member (e.g., concave vs. convex). In a particularly preferred form, the first members forming the diagonal elements are slightly longer than the second members. In another particularly preferred form, the elbows are all identical to one another, and each elbow has an approximately 90° orientation in the unexpanded state of the stent (as described below), and an approximately 130° orientation when the stent is in its expanded state (as described below).

Adjacent diagonal elements in each cylindrical ring are connected by cotter pin connectors. In particular, a cotter pin connector connects the first end of each first member to the first end of a second member in an immediately adjacent cell. When the stent is in its unexpanded state, the cotter pin connectors have a uniform radius of curvature forming a smooth transition from the first and second members to which they are connected. The smooth transition region between the first and second members and the cotter pin connectors provide less stress in the stent body than would be present with other than a smooth transition region. A plurality of relatively short longitudinal connectors connect adjacent cotter pin connectors, and thereby connect adjacent circumferential rings to integrate the stent body.

In a preferred embodiment, the first members, second members, and elbows are formed of members having approximately the same width throughout the body of the stent. In an alternative embodiment, the first members forming the diagonal elements have a greater thickness than the second members and the elbows. In this alternative embodiment, the first member width is from about 25% to about 50% greater than the width of the second members and elbows. For example, in a particularly preferred form, the first member width is approximately 0.004 inches, while the second member and elbow widths are approximately 0.003 inches. The differential in width between the diagonal element components provides an alternative balance of axial flexibility (useful prior to stent placement to negotiate vessel paths) and radial rigidity (useful after stent deployment to provide internal strength to the lumen).

In a still further preferred embodiment, all of the diagonal elements making up the majority of the stent body have identical dimensions to each other, with four such diagonal elements forming the boundaries of each cell of the mesh pattern making up the stent body. Thus, the stent comprises a repeating mesh pattern of identical diagonal elements having four distinct relative spatial orientations.

In a preferred form, the tubular body is a coiled-sheet, having overlapping inner and outer longitudinal sections. In a particularly preferred form, the coiled-sheet stent is provided having a maximum of 100% overlap in its coiled, unexpanded condition. For example, previous coiled sheet stents were formed of flat sheets having a width that generally corresponded to the desired circumference of the cylindrical stent upon expansion within the body lumen, plus an amount of overlap. The flat sheet was then rolled up or coiled into a cylinder having a relatively small diameter for delivery to the treatment site, where it was then radially enlarged to its expanded condition. Typically, the previous coiled sheet stents were coiled to the extent that the internal and exposed portions of the coiled sheet would overlap by 150% to 300% or more in order to provide sufficient expansion capacity to satisfactorily occupy the body lumen. In the preferred embodiment of the stent described herein, the amount of overlap between the internal and exposed portions of the coiled sheet is less than 100%, preferably between about 20% and about 100%, and most preferably between about 20% and about 50%. Limiting the degree of overlap results in a decrease in the friction force caused by and existing between the overlapping layers, which are in physical contact with one another. This friction force tends to prevent the coiled sheet from radially expanding from its contracted state to its expanded state. Thus, the reduction in friction force provided by the stent described herein allows the stent to expand more readily and decreases the possibility that the stent will fail to expand when it is placed in the treatment location.

For any coiled sheet stent having a given diameter in its contracted condition, a lesser degree of overlap will necessarily result in a relatively smaller amount of radial expansion capacity attributable to the uncoiling of the stent. Accordingly, in a preferred embodiment, the coiled sheet stent described herein includes a mesh pattern that provides an amount of radial expansion between the contracted (delivery) state and the expanded (engagement) state. In this way, radial expansion of the stent is provided by the dual actions of, first, uncoiling of the coiled sheet and, second, expansion of the mesh pattern. Examples of mesh patterns providing radial expansion of the coiled sheet stent are described herein, while others are known in the art.

Preferably, a plurality of teeth or fingers extend from an edge of the inner longitudinal section for engaging openings in the outer longitudinal section. Alternatively, the tubular body may be a plastically deformable or self-expanding tube.

The tubular body is generally expandable between a contracted condition for facilitating introduction into a body lumen, and an enlarged condition for engaging a wall of a body lumen. Preferably, the tubular body is biased toward the enlarged condition. More preferably, the zig-zag pattern is expandable between an unstretched condition and a stretched condition, the zig-zag pattern being biased towards the stretched condition above a transition temperature which is substantially below body temperature, thereby at least partially defining the enlarged condition. Thus, ends of adjacent diagonal elements may be arranged further away from one another about the circumference in the stretched condition than in the unstretched condition. Further, the diagonal elements may have a less arcuate shape in the stretched condition than in the unstretched condition such that the diagonal elements at least partially straighten for minimizing foreshortening of the tubular body along the longitudinal axis. The foreshortening minimizing effect may be enhanced through the use of a heat treatment process described herein in which the body of the stent is stretched both circumferentially and longitudinally in order to decrease the arcuate shape of the diagonal elements in the stretched condition.

In accordance with another aspect of the present invention, a stent is provided that has a multi-cellular mesh structure. The stent includes a generally tubular body having a longitudinal axis and a circumference, a plurality of generally bat shaped cells formed in the tubular body, each cell defining a head region, a tail region and opposing curved wing regions, and a plurality of connectors extending between and connecting adjacent cells.

Preferably, the head region of each cell is connected to the tail region of each circumferentially adjacent cell. For example, the head and tail regions may be directly connected together. Alternatively, a circumferential connector may be provided between the head and tail regions of adjacent cells. The plurality of connectors preferably include a connector extending between a wing region of a first cell and a wing region of an adjacent cell. Alternatively, the wing regions of adjacent cells may be directly connected together.

The cells may be provided in a variety of arrangements both about the circumference and along the longitudinal axis of the tubular body. For example, the head and tail regions may be aligned about the circumference, and the wing regions may have a generally "V" shape extending longitudinally away from the head and tail regions. Preferably, the cells are arranged sequentially about the circumference, thereby defining a cylindrical band. The tubular body may include a plurality of cylindrical bands, each including a sequence of bat shaped cells, adjacent cylindrical bands being connected to one another by longitudinal connectors.

In a preferred form, the wing regions are defined by first and second arcuate members, the first and second arcuate members including a first member and second member connected to one another by an elbow. Each head region may then be defined by a longitudinal connector extending between the first arcuate members of the opposing wing regions of the respective cell, and the tail region may be defined by a longitudinal connector extending between the second arcuate members of the opposing wing regions of the respective cell. More preferably, the longitudinal connector of the tail region also defines the longitudinal connector for the head region of an adjacent cell and the longitudinal connector of the head region defines the longitudinal connector for the tail region of an adjacent cell.

The curved wing regions or arcuate diagonal elements significantly improve the flexibility of the resulting stent. Conventional coiled-sheet stents, for example, have substantially rigid lattice structures which may not be as flexible transverse to the longitudinal axis of the stent as desired. In contrast, the arcuate diagonal elements of the stent described herein facilitate flexing of the individual cells generally transverse to the longitudinal axis, the arcuate diagonal elements extending or compressing as needed to facilitate bending of the stent. Thus, the stent may conform more easily to tortuous body regions through which the stent is directed or within which the stent is implanted. In addition, the arcuate diagonal elements may also reduce foreshortening of the stent during expansion.

In accordance with still another aspect of the present invention, a coiled sheet stent is provided having a flexible mesh pattern of cells formed from diagonal elements, cotter pin connectors, and longitudinal connectors. Each cell of the mesh pattern is defined by four diagonal elements: a first pair connected by a first cotter pin connector and a second pair, opposed to the first, connected by a second cotter pin connector. First and second longitudinal connectors at the top and bottom of the cell complete the cell, with the top longitudinal connector of a first cell comprising also the bottom longitudinal connector of the above-adjacent cell. The resultant cell, defined by its structural components, has a generally symmetrical, bat-shaped appearance.

An advantage provided by the coiled sheet stents described herein is an improved balance of longitudinal flexibility and radial rigidity. For example, the coiled sheet stents described herein preferably incorporate a continuous mesh pattern having no discontinuities or discontinuous sections. The continuous mesh pattern provides a greater amount of radial rigidity when the stent is in its expanded state relative to a non-continous mesh pattern. Whereas prior art continuous mesh designs have suffered from a lack of longitudinal flexibility, particularly upon bending, the continuous mesh designs described herein provide relatively less bottom-compression and top-tension than those stents due to the described mesh pattern.

In accordance with still another aspect of the present invention, a method of manufacturing a coiled sheet stent having little or no longitudinal foreshortening as it expands includes a step of imparting a shape memory to a flat sheet forming the stent body to cause expansion of the stent body in a dimension other than circumferentially, and particularly longitudinally. In a preferred method, the flat sheet of shape memory material, such as Nitinol, is stretched along its circumferential plane by applying a stretching force to the opposed longitudinal edges of the sheet, and is stretched along its longitudinal plane by applying a stretching force to the opposed ends of the sheet. The stretched sheet is heated to a temperature of about 450° C. to about 550° C. for about 2 to about 30 minutes.

Other objects and features of the present invention will become apparent from consideration of the following description taken in conjunction with the accompanying drawings.

BRIEF DESCRIPTION OF THE DRAWINGS

Numeral references are employed to designate like parts throughout the various figures of the drawing.

DETAILED DESCRIPTION OF THE PREFERRED EMBODIMENTS

Figure 1A:
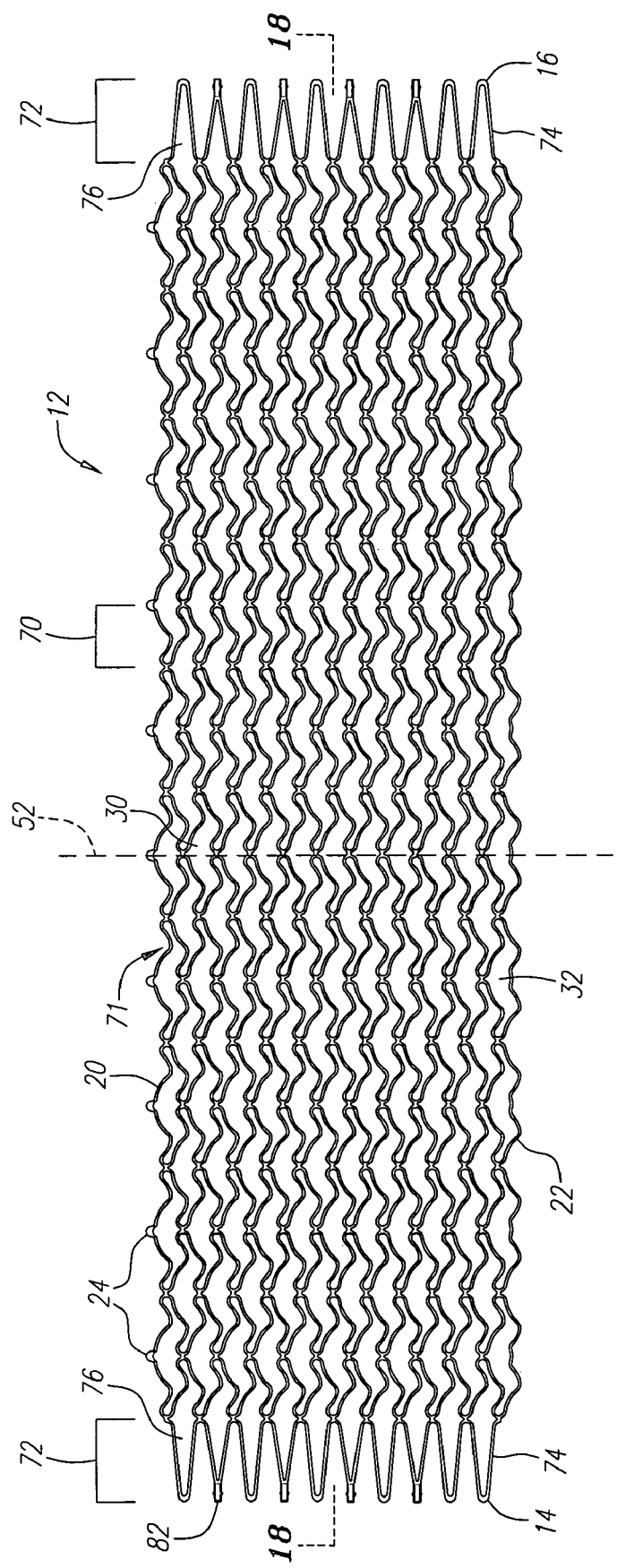
FIG. 1A is a side view of an unrolled coiled-sheet for a stretchable coiled-sheet stent, in accordance with one aspect of the present invention.
Figure 1B:
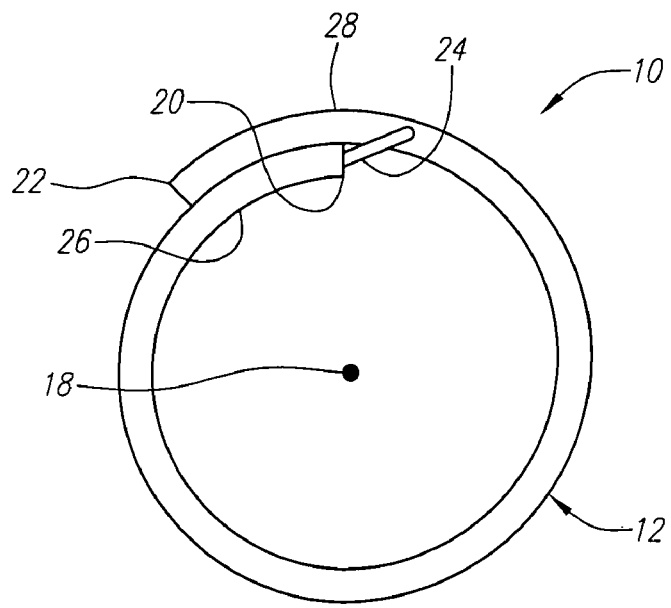
FIG. 1B is an end view of the coiled-sheet of FIG. 1A rolled into a coiled-sheet stent.

Turning now to the drawings, FIGS. 1A and 1B show a preferred embodiment of a coiled-sheet stent 10, in accordance with one aspect of the present invention. The coiled-sheet stent 10 is formed from a substantially flat sheet 12 having first and second ends 14, 16 defining a longitudinal axis 18 therebetween. The sheet 12 also includes first and second longitudinal edges 20, 22, the first edge 20 having a plurality of fingers or teeth 24 extending therefrom substantially perpendicular to the longitudinal axis 18.

The sheet 12 also includes a plurality of stretchable elements 30 formed therein, thereby defining a multi-cellular mesh structure capable of expanding and/or contracting in a direction substantially perpendicular to the longitudinal axis 18. Preferably, the stretchable elements 30 define a lattice-like structure providing a plurality of openings 32 for receiving the teeth 24, as described further below. Thus, each stretchable element generally defines an individual "cell," thereby providing a multi-cellular structure when the individual cells are duplicated in a predetermined pattern, as in the preferred embodiments described herein. The stretchable elements 30 may be elastically deformable, i.e., biased to assume a first shape but temporarily deformable from that first shape, and/or may be plastically deformable, i.e., assuming any shape to which the stretchable elements 30 are deformed.

As used herein, the terms "longitudinal" and "longitudinally" refer to those elements oriented towards the ends of the stent, i.e., arranged generally along the longitudinal axis. The terms "circumferential" and "circumferentially" refer to those elements oriented about the periphery or circumference of the stent, i.e., arranged generally perpendicular to the longitudinal axis As best seen in FIG. 1B, the sheet 12 is preferably provided in a coiled-up condition, defining overlapping inner and outer longitudinal sections 26, 28 that may slide with respect to one another to allow radial expansion of the coiled-sheet 12 between a contracted condition and one or more enlarged conditions. In the preferred embodiment, the amount of overlap between the overlapping inner and outer longitudinal sections 26, 28 is from about 20% to about 100%, and most preferably between about 20% and about 50%, relative to the circumference of the tubular body formed by the coiled-up sheet in its contracted condition. The coiled-up sheet 12 may be biased to the contracted condition, thereby requiring a balloon or other expandable member to radially expand the stent 10 to the In a preferred form, the stretchable elements 30 have a temperature-activated shape memory. For example, at a first temperature, the stretchable elements 30 may be biased to assume a circumferentially contracted or "unstretched" shape, while at a higher second temperature, e.g., above a transition temperature for the stent material, the stretchable elements 30 may become biased to assume a circumferentially expanded or "stretched" shape. Preferably, the first temperature is substantially below ambient temperature, such as about −20° C., and the second temperature is substantially below body temperature, such as no more than 28° C., and preferably about 18-20° C.

To manufacture a coiled-sheet stent 10 as described, a relatively thin, substantially flat sheet 12 is provided formed from a biocompatible material, such as stainless steel or a polymer. More preferably, the sheet 12 is formed from a shape memory polymer or metal, such as a nickel-titanium alloy ("Nitinol"), more preferably having a thermally-activated shape memory. Alternatively, an elastic material, such as tantalum, platinum or tungsten alloy, or a super-elastic material, such as Nitinol, may be used. The stretchable elements 30, the teeth 24 and/or any other openings in the sheet 12 may be formed using a number of conventional metal working processes, such as die and punch, laser cutting, or chemical etching.

In one preferred method, the stretchable elements 30 are formed in their stretched shape and the sheet 12 is subsequently heat treated, for example, to a temperature of about 450° C. or higher, to activate the shape memory of the material. After the sheet 12 has cooled, the stretchable elements 30 are compressed into their unstretched shape, and the sheet 12 is rolled to provide a coiled-sheet stent 10.

Preferably, the sheet is formed from Nitinol which, when heat treated, is converted substantially to its austenitic phase, i.e., set to assume its stretched shape. As it is cooled, the Nitinol material preferably undergoes martensitic transformation. When the stretchable elements 30 are compressed into their unstretched shape at low temperatures relative to ambient, such as about −20° C., the material is substantially martensite which is plastically deformed into the unstretched condition. More preferably, a Nitinol alloy is selected such that transformation back to austenite occurs well before the time the material reaches body temperature, e.g., about 18-20° C. Thus, the stretchable elements 30 may automatically become biased to resume the stretched shape prior to reaching body temperature.

In another preferred method, the stretchable elements 30 may be formed in their unstretched shape, and then plastically deformed to their stretched shape, e.g., while the Nitinol material is in its martensitic phase. The sheet 12 may then be heat treated, e.g., to transform the material to its austenitic phase, thereby storing the stretched shape in the material's shape memory. Upon cooling, the material will transform back to martensite, thereby returning to the unstretched shape. The sheet 12 may then be rolled into its contracted condition for placement on a delivery device (not shown).

Figure 4:
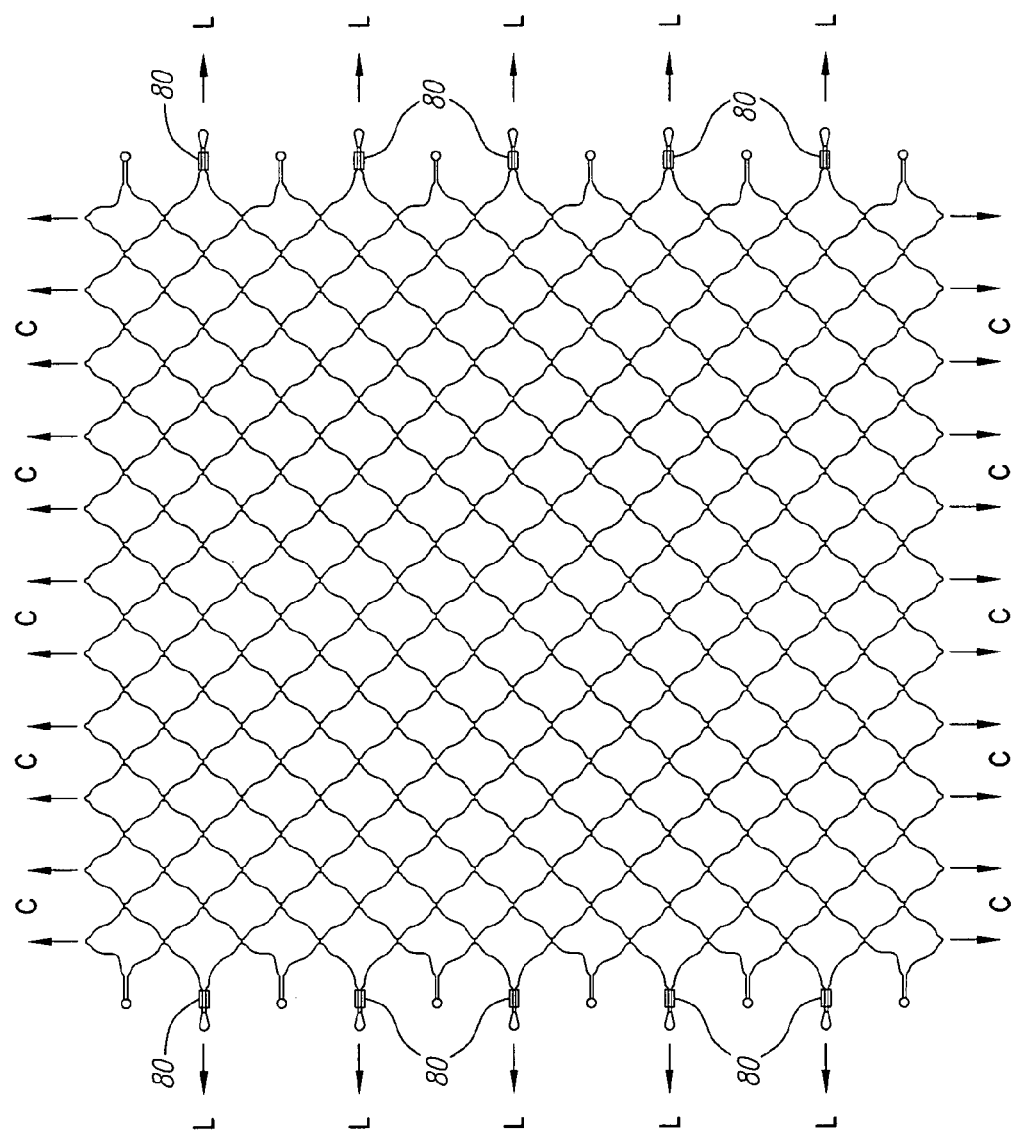
FIG. 4 is a side view of an unrolled coiled-sheet for a stretchable coiled-sheet stent, in accordance with another aspect of the present invention.

Turning to FIG. 4, in another preferred method, the stretched shape of the stretchable elements 30 is formed by applying a stretching force over more than one planar dimension of the unrolled coiled sheet. For example, in prior coiled sheet stents formed from shape memory material, it was known to apply a stretching force in the circumferential dimension in order to provide a circumferential expansion bias to the coiled sheet. In the preferred method of the present invention, a stretching force is applied to the coiled sheet in the circumferential dimension (see arrows C in FIG. 4) and in at least one other dimension, preferably longitudinally (see arrows L in FIG. 4). The non-circumferential stretching force has the effect of causing or enhancing expansion in the non-circumferential dimension when the coiled sheet expands from its contracted state to its expanded state. Thus, if the non-circumferential dimension is longitudinal, the non-circumferential stretching force has the effect of causing or enhancing longitudinal expansion, which will tend to decrease or eliminate foreshortening of the stent upon expansion, as discussed below.

As shown in FIG. 4, in a preferred method, the longitudinal stretching force may be applied by grasping alternating (i.e., every other) terminal strut ends and applying the stretching force to the grasped strut ends. The strut ends that are grasped tend to elongate to a greater degree than the non-grasped ends in the terminal row of cells. The non-grasped terminal row cells, on the other hand, tend to compensate for the elongation of the grasped terminal row cells by flattening—i.e., causing the cell to extend in the circumferential direction to a greater degree than the adjacent elongated cells. The result is a reduction in the foreshortening of the stent as measured by the ends of the elongated (grasped) terminal row cells.

Preferably, sleeve stent markers 80 may be located on the extended strut edges. The sleeve stent markers are described more fully in published U.S. Patent Application 2004/0254637, entitled "Sleeve Stent Marker," assigned to Endotex Interventional Systems, Inc., and filed on the same date as the present application. The aforementioned patent application is hereby incorporated by reference in its entirety as if fully set forth herein.

The coiled-sheet stent 10, in its contracted condition, may be placed over the distal end of a delivery catheter (not shown) having a size adapted for percutaneous introduction into a patient's vasculature. A retractable sheath (not shown) may be advanced over the distal end, thereby protecting the stent 10, preventing shifting and/or preventing premature deployment. Alternatively, other mechanisms may be provided for constraining the stent 10 in its contracted condition, such as a wire or thread (not shown) which may be woven through overlapping layers of the stent to prevent premature unrolling.

The distal end of the catheter-sheath assembly may then be percutaneously introduced into a patient's vasculature, and advanced to a target treatment location, such as a stenosis within the carotid or coronary arteries. The transition temperature of the stent material is surpassed either prior to or during introduction (unless some form of temperature control is utilized), thereby activating the temperature-activated shape memory of the material such that the stretchable elements 30 become biased to assume their stretched shape, e.g., when the Nitinol completes transformation back to austenite. Thus, the sheath constrains the stent 10 from at least partially expanding because of the stretching of the stretchable elements 30. Once the stent 10 is properly positioned at the treatment location, the sheath may be retracted, thereby exposing the stent 10, which may then at least partially expand radially as the stretchable elements 30 assume their stretched shape.

The catheter-sheath assembly may be withdrawn, and a balloon catheter (not shown) may be introduced into the interior of the partially expanded stent 10. Alternatively, a balloon or other expandable member (not shown) may be provided on the delivery catheter adjacent to the stent 10. The balloon may be inflated, thereby further radially expanding the stent 10. Once a desired enlarged condition is achieved, the balloon is deflated and withdrawn. Preferably, the teeth 24 on the inner longitudinal edge 20 engage a set of the openings 32 in the sheet 12, thereby substantially locking the stent 10 in its enlarged condition. Thus, the teeth 24 allow the stent 10 to be ratcheted to a number of enlarged conditions as long as the inner and outer longitudinal sections 26, 28 overlap and allow the teeth 24 to engage corresponding openings 32, as will be appreciated by those skilled in the art.

In addition, the coiled-sheet stent may also include outwardly-oriented hooks or barbs (not shown) for enhancing anchoring of the stent within a body passage. Pro-thrombotic material (not shown) may be provided on the exterior surfaces of the coiled-sheet stent to enhance sealing against the wall of the body passage. Additional information on coiled-sheet stents appropriate for use with the present invention may be found, for example, in U.S. Pat. No. 4,577,631 issued Mar.

25, 1986 in the name of Kreamer, U.S. Pat. No. 5,007,926 issued Apr. 16, 1991 in the name of Derbyshire, U.S. Pat. No. 5,158,548 issued Oct. 28, 1992 in the name of Lau et al., U.S. Re. Pat. No. 34,327 reissued Jul. 27, 1993 in the name of Kreamer, U.S. Pat. No. 5,423,885 issued Jun. 13, 1995 in the name of Williams, U.S. Pat. No. 5,441,515 issued Aug. 15, 1995 in the name of Khosravi et al., and U.S. Pat. No. 5,443,500 issued Aug. 22, 1995 in the name of Sigwart. The disclosures of these references and any others cited therein are expressly incorporated herein by reference.

The stretchable elements included in a coiled-sheet stent in accordance with the present invention may take on a number of different forms. Generally, a plurality of stretchable elements are provided in a predetermined arrangement, such as a longitudinal or circumferential configuration, although a variety of arrangements providing a desired recoil or flexibility characteristic may be provided. U.S. Pat. No. 6,325,820, the disclosure of which is expressly incorporated herein by reference, discloses a number of such arrangements.

Figure 2:
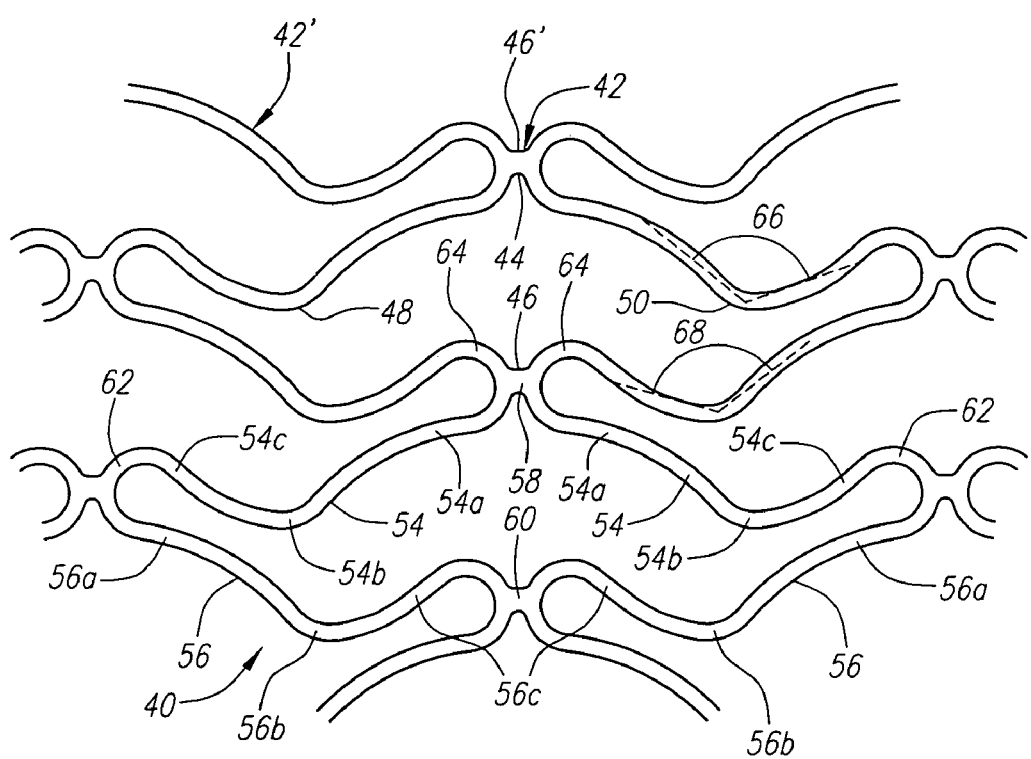
FIG. 2 is a detail of a preferred embodiment of a stretchable cell structure.

Turning to FIG. 2, a preferred embodiment of a multicellular mesh structure 40 is shown which includes a plurality of cells 42 having a shape which may be described as similar to a bat. Each cell 42 defines a "head" region 44, a "tail" region 46, and first and second curved "wing" regions 48, 50 which make up the bat shape. The head region 44 of each cell is connected to the tail region 46' of the adjacent cell 42'. Preferably, the adjacent cells 42, 42' are directly connected, as shown, although alternatively, one or more circumferential connectors (not shown) may be provided that extend circumferentially between the adjacent head and tail regions.

The head and tail regions 44, 46 are preferably aligned circumferentially, i.e., defining a circumferential axis 52 (see FIG. 1A) substantially perpendicular to the longitudinal axis 18, and the wing regions 48, 50 preferably have a generally "V" shape extending longitudinally away from the head and tail regions 46, 48, i.e., opposing one another about the circumferential axis 52.

The wing regions 48, 50 are preferably defined by first and second arcuate members 54, 56, the arcuate members 54, 56 each including a first member 54a, 56a and a second member 54c, 56c connected to one another by an elbow 54b, 56b. Preferably, the second member 54c is substantially shorter than the first member 54a of the first arcuate member 54, and similarly, the second member 56c is substantially shorter than the first member 56a of the second arcuate member 56, as may be seen in FIG. 2. Each head region 44 is preferably defined by a longitudinal connector 58 extending between the first members 54a of the first arcuate members 54 of the opposing wing regions 48, 50. Similarly, the tail region is preferably defined by a longitudinal connector 60 extending between the second members 56c of the second arcuate members 56.

Preferably, the ends of the first members 56a of the second arcuate members 56 opposite the elbows 56b are connected to the ends of the second members 54c of the first arcuate members 54 by a cotter pin connector 62, thereby defining tips of the wing regions 48, 50. In addition, the ends of the first members 54a of the first arcuate members 54 opposite the elbows 54b are connected to the ends of the second members 56c of the circumferentially adjacent cells 42 by cotter pin connectors 64. This structure results in the longitudinal connector 58 of the head region 44 also being the longitudinal connector for the tail region 46 of the adjacent cell 42 and the longitudinal connector 60 of the tail region 46 being the longitudinal connector for the circumferentially adjacent head region 44.

Figure 3:
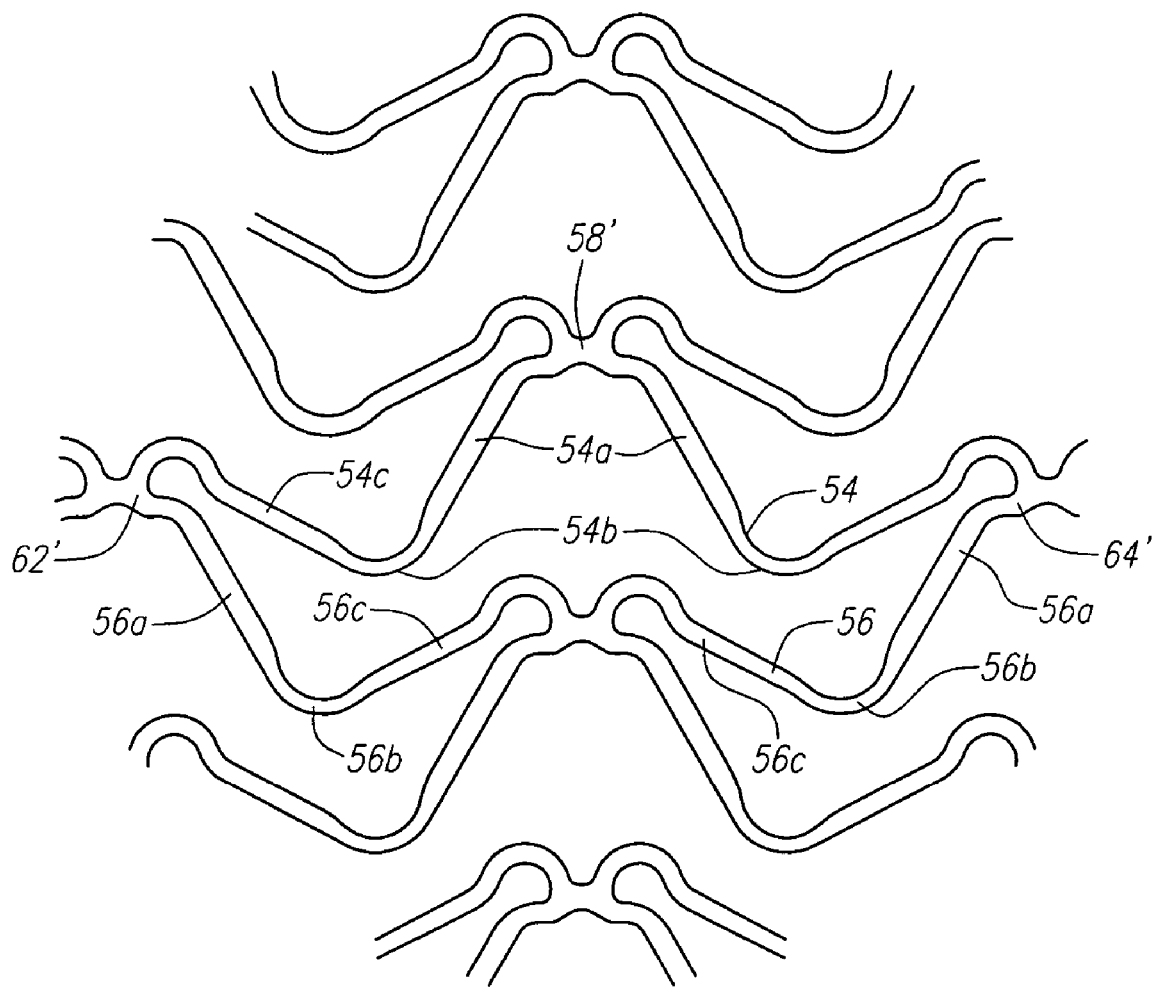
FIG. 3 is a detail of another preferred embodiment of a stretchable cell structure.

In the embodiment shown in FIG. 2, the arcuate members and elbows generally have constant width. In an alternative embodiment, shown in FIG. 3, the shorter second members 54c and elbows 54b have a smaller width than the longer first members 54a. In the preferred form, the longer first members have about 25% to about 50% greater width, and most preferably about 33% greater width, than the shorter second members and elbows. The mesh structure shown in FIG. 3 also includes a slightly modified form of the cotter pin connectors 62', 64', having a bulbous form rather than a constant radius of curvature having a smooth transition with the first and second members. Additionally, the FIG. 3 mesh structure includes a longitudinal connector 58' that is shifted circumferentially downward (as shown in the Figures) relative to the location shown in FIG. 2.

As shown in FIGS. 1A and 1B, when a sheet 12 having bat shaped cells formed therein (not shown) is rolled into a coiled-sheet stent 10, each circumferential sequence of wing regions 48, 50 defines a cylindrical band 70. Each cylindrical band 70 has a generally zig-zag pattern defined by a series of sequential diagonal elements, namely the alternating first and second arcuate members 54, 56, connected to one another by cotter pin connectors 62, 64.

Within each cylindrical band, 70, all of the diagonal elements 54, 56 are preferably oriented in either a "clockwise" or "counter-clockwise" direction about the circumference. Stated differently, the elbows 54b, 56b are all aligned in each band 70 such that they generally "point" in a single direction about the longitudinal axis 18, as viewed from FIG. 1B, for example, or parallel to the circumferential axis 52, as viewed from FIG. 1A. Thus, the elbows 54b, 56b define apices in the generally "V" shaped wing regions 48, 50 which point about the longitudinal axis 18 in either a clockwise or counter-clockwise direction. This feature facilitated "packing" of the diagonal elements 54, 56 in each cell with one another, i.e., for compressing the diagonal elements 54, 56 when the coiled-sheet stent is in its unstretched condition without causing overlapping of the diagonal elements 54, 56.

More preferably, all of the diagonal elements 54, 56 in all of the cells of the stent are preferably oriented clockwise, as viewed from FIG. 1B. Thus, the elbows 54b, 56b of underlying diagonal elements 54, 56 may be oriented away from overlying diagonal elements 54, 56, which may substantially reduce the risk of underlying diagonal elements catching on overlying diagonal elements during expansion.

The arcuate diagonal elements (or curved wing regions) provide flexibility to the overall mesh structure of the coiled-sheet stent. Coiled-sheet stents having rigid grid mesh structures may not provide sufficient flexibility generally transverse to the longitudinal axis of the stent. In contrast, the arcuate diagonal elements allow the individual cells to flex generally transverse to the longitudinal axis, the arcuate diagonal elements extending or compressing as needed. Thus, the stent may conform more easily to tortuous body regions through which the stent is directed or within which the stent is implanted.

In addition, the arcuate diagonal elements may also reduce foreshortening of the stent during expansion. Diamond shaped mesh structures, for example, may substantially foreshorten longitudinally as they expand radially. The cell structures of the stents described herein, in contrast, may substantially reduce such foreshortening. During expansion, adjacent diagonal elements move away from one another in the circumferential direction, i.e., parallel to the circumferential axis 52, thereby tending to reduce the longitudinal component of the diagonal elements. To compensate for at least some of this reduction, the elbows 54b, 56b of the diagonal elements 54, 56 may yield, increasing an inside angle 66, 68 between the first and second members 54a, 56a, 54c, 56c of the respective diagonal elements 54, 56 and thereby increasing the longitudinal component of the diagonal elements 54, 56. This effect is caused or enhanced by utilizing the heat treatment methods described herein.

In a preferred form, the longitudinal connectors 58, 60 have a length that is substantially less than the longitudinal component of the arcuate diagonal elements 54, 56, thereby ensuring effective scaffolding of the body lumen during expansion. Alternatively, the longitudinal connectors 58, 60 may have a length as long as or greater than the longitudinal component of the diagonal elements 54, 56, although this may be disfavored because of the gaps that may occur within the multicellular structure.

In a further alternative, the longitudinal connectors may include curved portions that may provide additional flexibility between the adjacent cylindrical cells. The flexible nature of the arcuate diagonal elements and curved wing regions, however, preferably provide sufficient flexibility such that substantially straight longitudinal connectors may be provided that extend substantially parallel to the longitudinal axis. The longitudinal connectors may bend, either where they connect to the diagonal elements or at an intermediate point, when the stent is bent transverse to the longitudinal axis to provide additional flexibility.

In the embodiment shown in FIG. 1A, the stent body includes a center portion 71 formed of the mesh structure comprising bat shaped cells as described above with respect to FIG. 2, and a terminal cylindrical band 72 at each of the first and second ends 12, 14. The terminal cylindrical bands 72 comprise a zig-zag pattern of straight sections 74 forming half-diamond or triangular-shaped cells 76. A slot 82 is shown in alternating ones of the terminal ends of the struts making up the terminal cylindrical bands. The slots 82 facilitate the attachment of a sleeve marker to the stent, as described more fully in the "Sleeve Stent Marker" patent application described above. In an alternative embodiment, such as that shown in FIG. 4, the entire stent body is formed of the mesh structure comprising bat shaped cells, and the terminal cylindrical bands 72 are not included.

The coiled sheet stents and methods are described herein and illustrated in the attached drawings in terms of several features of the stents and methods. It is intended and it should be understood that those features may be combined in many different ways to obtain the benefits described herein, and that the specific features and examples described herein are presented for illustrative purposes and are not intended to be limiting.

Furthermore, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A stent comprising:
    a coiled sheet having a longitudinal axis and first and second longitudinal edges, said coiled sheet having an unexpanded condition and an expanded condition, wherein said first and second longitudinal edges have a circumferential overlap of about 20% to about 100% when the coiled sheet is in the unexpanded condition;
    a plurality of cylindrical bands formed in said coiled sheet, each cylindrical band comprising a generally zig-zag pattern comprising a series of sequential diagonal elements connected to one another,
    a first terminal band, and a second terminal band, the first terminal band being distal of the plurality of cylindrical bands and the second terminal band being proximal of the plurality of cylindrical bands, the first and second terminal bands comprising a plurality of straight sections, pairs of straight sections being engaged to form terminal ends, at least one of the terminal ends being a slot terminal end, the slot terminal end defining a through hole, the through hole having a length;
    at least one stent sleeve marker, the at least one stent sleeve marker having a length less than the length of the through hole, the marker having a first end and a second end, the first and second ends being open, the marker having a first portion, one of the slot terminal ends being disposed within each marker so that the marker is centered over the slot, the first portion of the marker being depressed into the through hole thereby engaging the maker to the slot terminal end and
    a plurality of longitudinal connectors extending between and connecting adjacent cylindrical bands.

2. The stent of claim 1, wherein the coiled sheet is expandable between the unexpanded condition for facilitating introduction into a body lumen and the expanded condition for engaging a wall of a body lumen.

3. The stent of claim 2, wherein the coiled sheet is biased towards the expanded condition.

4. The stent of claim 2, wherein the zig-zag pattern is expandable between an unstretched condition and a stretched condition, the zig-zag pattern being biased towards the stretched condition above a transition temperature which is substantially below body temperature, thereby at least partially defining the expanded condition.

5. The stent of claim 4, wherein ends of adjacent diagonal elements are arranged further away from one another about the circumference in the stretched condition than in the unstretched condition.

6. The stent of claim 5, wherein the diagonal elements have a less arcuate shape in the stretched condition than in the unstretched condition such that the diagonal elements at least partially straighten for minimizing foreshortening of the coiled sheet along the longitudinal axis.

7. The stent of claim 1, wherein all of the diagonal elements in all of the bands comprising the coiled sheet are oriented in a clockwise direction about the circumference.

8. The stent of claim 1, wherein the longitudinal connectors have a longitudinal dimension which is substantially smaller than a longitudinal dimension of the diagonal elements.

9. The stent of claim 1, wherein each diagonal element comprises first and second generally straight portions having first and second ends, the second ends being connected together by a curved portion, the first ends being connected to preceding and succeeding diagonal elements.

10. The stent of claim 1, wherein the diagonal elements of each cylindrical band are out of phase with any adjacent cylindrical band.

11. The stent of claim 1, at least one of the terminal strut ends being elongated compared to other of the terminal strut ends.

12. The stent of claim 11, the elongated terminal strut ends having a stent sleeve marker engaged thereto.

13. The stent of claim 1, the terminal strut end, to which a stent sleeve marker is engaged, having a slot.

14. A stent, the stent comprising a plurality of arcuate members and a plurality of longitudinal connectors, the plurality of arcuate members and the plurality of longitudinal connectors defining a plurality of cells, each of the plurality of cells having a first wing region, a second wing region, a head region and a tail region, the first wing region extending longitudinally away from the proximal ends of head and tail regions, the second wing region extending longitudinally away from the distal ends of the head and tail regions, each wing region being defined by two arcuate members engaged to one another, each head and tail region being defined by a longitudinal connector, each arcuate member comprising a first member, a second member and an elbow, the elbow engaging the first and second members, the first member having a first curvature, the second member having a second curvature, the first curvature being opposite to the second curvature, the first member having a first length and the second member having a second length, the first length greater than the second length, the first member having a first width, the second member having a second width and the first elbow having a third width, the first width being greater than the second and third widths.

15. The stent of claim 14, the first width being about 25% to about 50% greater than the second and third widths.

16. The stent of claim 14, the first elbows each having about an 90 degree orientation when the stent is in an unexpanded state and the first elbows each having about an 130 degree orientation when the stent is in an expanded state.

17. A stent, the stent comprising a plurality of arcuate members and a plurality of longitudinal connectors, the plurality of arcuate members and the plurality of longitudinal connectors defining a plurality of cells, each of the plurality of cells having a first wing region, a second wing region, a head region and a tail region, the first wing region extending longitudinally away from the proximal ends of head and tail regions, the second wing region extending longitudinally away from the distal ends of the head and tail regions, each wing region being defined by two arcuate members engaged to one another, each head and tail region being defined by a longitudinal connector, each arcuate member comprising a first member, a second member and an elbow, the elbow engaging the first and second members, the first member having a first curvature, the second member having a second curvature, the first curvature being opposite to the second curvature, each arcuate member having a longitudinal dimension, each longitudinal connector having a longitudinal dimension, the longitudinal dimension of the longitudinal connectors being less than the longitudinal dimension of the arcuate members.

18. The stent of claim 17, the plurality of cells forming a plurality of cylindrical bands, the cells of adjacent cylindrical bands being circumferentially offset from one another.

19. A stent, the stent comprising a plurality of arcuate members and a plurality of longitudinal connectors, the plurality of arcuate members and the plurality of longitudinal connectors defining a plurality of cells, each of the plurality of cells having a first wing region, a second wing region, a head region and a tail region, the first wing region extending longitudinally away from the proximal ends of head and tail regions, the second wing region extending longitudinally away from the distal ends of the head and tail regions, each wing region being defined by two arcuate members engaged to one another, each head and tail region being defined by a longitudinal connector, each arcuate member comprising a first member, a second member and an elbow, the elbow engaging the first and second members, the first member having a first curvature, the second member having a second curvature, the first curvature being opposite to the second curvature, the stent further comprising at least one stent marker, the at least one stent marker being a hollow tube, a portion of the plurality of arcuate members forming an end of the stent, the portion of the plurality of arcuate members comprising a first arcuate member and a second arcuate member, the first and second arcuate member defining a wing region of one of the plurality of cells, the at least one stent marker being engaged to the first and second arcuate members so that the stent marker surrounds a portion of an exterior surface of the first and second arcuate members and extends between the first and second arcuate members.

20. A stent, the stent comprising a plurality of arcuate members and a plurality of longitudinal connectors, the plurality of arcuate members and the plurality of longitudinal connectors defining a plurality of cells, each of the plurality of cells having an unexpanded configuration and an expanded configuration;
  each of the plurality of cells in the unexpanded configuration being bat shaped, the bat shaped cell comprising a first wing region, a second wing region, a head region and a tail region, the first wing region extending longitudinally away from the proximal ends of the head and tail regions and the second wing region extending longitudinally away from the distal ends of the head and tail regions, each wing region being defined by a first arcuate member engaged to a second arcuate member by a cotter pin connector, the head region being defined by a first longitudinal connector and the tail region being defined by a second longitudinal connector;
  each of the plurality of cells in the expanded configuration being substantially square shaped.

* * * * *